(12) United States Patent
Bodor

(10) Patent No.: US 10,335,367 B2
(45) Date of Patent: *Jul. 2, 2019

(54) USE OF SELECTED ANTICHOLINERGIC ZWITTERIONS

(71) Applicant: Bodor Laboratories, Inc., Miami, FL (US)

(72) Inventor: Nicholas S. Bodor, Bal Harbour, FL (US)

(73) Assignee: BODOR LABORATORIES, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/757,534

(22) PCT Filed: Aug. 26, 2016

(86) PCT No.: PCT/US2016/049047
§ 371 (c)(1),
(2) Date: Mar. 5, 2018

(87) PCT Pub. No.: WO2017/040307
PCT Pub. Date: Mar. 9, 2017

(65) Prior Publication Data
US 2018/0243209 A1    Aug. 30, 2018

Related U.S. Application Data

(63) Continuation of application No. 14/845,645, filed on Sep. 4, 2015.

(51) Int. Cl.
| | |
|---|---|
| *A61K 31/40* | (2006.01) |
| *A61P 27/10* | (2006.01) |
| *A61K 9/00* | (2006.01) |
| *C07D 207/12* | (2006.01) |

(52) U.S. Cl.
CPC ............ *A61K 9/0048* (2013.01); *A61K 31/40* (2013.01); *A61P 27/10* (2018.01); *C07D 207/12* (2013.01)

(58) Field of Classification Search
CPC ....... A61K 31/40; A61K 9/0048; A61P 27/10; A61P 27/02
See application file for complete search history.

(56) References Cited

U.S. PATENT DOCUMENTS

| | | |
|---|---|---|
| 6,433,003 B1 | 8/2002 | Bobrove et al. |
| 7,399,861 B2 | 7/2008 | Bodor |
| 7,417,147 B2 | 8/2008 | Bodor |
| 8,071,639 B2 | 12/2011 | Bodor |
| 8,147,809 B2 | 4/2012 | Bodor |
| 8,568,699 B2 | 10/2013 | Bodor |
| 9,220,707 B2 | 12/2015 | Bodor et al. |
| 2003/0064040 A1 | 4/2003 | Lukacsko |
| 2007/0123557 A1 | 5/2007 | Bodor |
| 2009/0257969 A1 | 10/2009 | Bodor |
| 2010/0114309 A1 | 5/2010 | De Juan et al. |
| 2012/0141401 A1 | 6/2012 | Bodor |
| 2014/0151255 A1 | 6/2014 | Johnston et al. |
| 2014/0275204 A1 | 9/2014 | Bodor et al. |
| 2015/0374621 A1 | 12/2015 | Bodor |

FOREIGN PATENT DOCUMENTS

| | | |
|---|---|---|
| JP | 2007-308398 | 11/2007 |
| WO | 2014/144075 | 9/2014 |

OTHER PUBLICATIONS

International Search Report and Written Opinion of the International Searching Authority dated Nov. 16, 2016, issued in corresponding International Application No. PCT/US2016/049047, 9 pages.
Wu, Whei-Mei et al., "Pharmacokinetic and Pharmacodynamic Evaluations of the Zwitterionic Metabolite of a New Series of N-Substituted Soft Anticholinergics", Pharmaceutical Research, vol. 22, No. 12, pp. 2035-2044, Dec. 12, 2005, Kluwer Academic, Plenum Publishers.
Fang, Yun-tuan et al., "Prescription of atropine eye drops among children diagnosed with myopia in Taiwan from 2000 to 2007: a nationwide study", Eye, vol. 27, No. 3, pp. 418-424, Macmillan Publishers (Jan. 2013).
Chia, Audrey et al., Atropine for the Treatment of Childhood Myopia: Safety and Efficacy of 0.5%, 0.1 % and 0.01 % Doses (Atropine for the Treatment of Myopia 2), Ophthalmology, vol. 119, No. 2, pp. 347-354, American Academy of Ophthalmology, Elsevier Inc. (Sep. 2011).
Chua, Wei-Han et al., "Atropine for the Treatment of Childhood Myopia", Ophthalmology, vol. 113, No. 12, pp. 2285-2291, American Academy of Ophthalmology, Elsevier Inc. (Dec. 2006).
Wu, Whei-Mei et al., "Stereoisomers of N-substituted soft anticholinergics and their zwitterionic metabolite based on glycopyrrolate-syntheses and pharmacological evaluations", Die Pharmazie—An International Journal of Pharmaceutical Sciences, vol. 63, No. 3, pp. 200-209 (Mar. 1, 2008).
Cooper, Jeffrey et al., "Current Status on the Development and Treatment of Myopia", Optometry, vol. 83, No. 5, pp. 174-199 (May 31, 2012).
International Search Report and Written Opinion of the International Searching Authority dated Jun. 12, 2015, issued in corresponding International Application No. PCT/US2015/020137, 8 pages.
International Search Report and Written Opinion of the International Searching Authority dated Oct. 13, 2016, issued in corresponding International Application No. PCT/US2016/043380, 7 pages.
Kirk et al., "Esterification and Esters, Organic", Kirk-Othmer Encyclopedia of Chemical Technology, 4th ed., Feb. 1994, vol. 9, pp. 1-24. ISBN-10 0471526770. http://vigoschools.org/~mmc3/AP%20Lab/ap%20lab%20documents/Esterification.pdf.
Non-Final Office Action dated Mar. 2, 2017 in corresponding U.S. Appl. No. 14/845,645, 8 pages.
Final Office Action dated Jun. 21, 2017 in corresponding U.S. Appl. No. 14/845,645, 10 pages.
Notice of Allowance dated Jul. 24, 2018 in corresponding U.S. Appl. No. 14/845,645, 8 pages.
Walline, Jeffrey J. et al.,"Interventions to slow progression of myopia in children", Cochrane Database Systematic Reviews, vol. 12, 103 pages (2011).
Office Action dated Dec. 12, 2018 in Japanese Patent Application No. 2016-556253, 8 pages.

*Primary Examiner* — Theodore R. West
(74) *Attorney, Agent, or Firm* — Dentons US LLP

(57) ABSTRACT

Selected anticholinergic zwittehons are administered to slow the progression of myopia in children and to treat myopia generally.

18 Claims, No Drawings

USE OF SELECTED ANTICHOLINERGIC ZWITTERIONS

CROSS REFERENCE TO RELATED APPLICATIONS

This application is the U.S. National Stage of International Patent Application No. PCT/US2016/049047, filed Aug. 26, 2016, which is a Continuation of U.S. application Ser. No. 14/845,645, filed Sep. 4, 2015, said earlier applications being assigned to the assignee hereof and also being incorporated by reference herein in their entireties and relied upon.

BACKGROUND

Technical Field

This application relates to methods for treating and/or for slowing the progression of myopia, particularly in children. These methods comprise administering a member of a selected group of anticholinergic zwitterions.

Description of Background Art

Myopia, also known as nearsightedness, is a common ocular disorder in humans. In the United States and Europe, myopia affects from 25% to 60% of older adults. The incidence is much higher in East Asia, where it can affect up to 80% of young adults. It typically occurs first in childhood.

Unfortunately, myopia is associated with increased risk of very serious conditions, among them glaucoma, detachment of the retina and myopic macular degeneration. Further, the incidence of myopia appears to be on the rise. It would therefore be of interest to develop an effective treatment of myopia, particularly one that can slow the progression of myopia, especially severe myopia, in children.

A review article on the present status of myopia treatment has been published recently by Jeffrey Cooper, Erica Schulman and Nadine Jamal. See Cooper et al., "Current Status on the Development and Treatment of Myopia", *Optometry* 2012 May 31, 83(5), pp. 174-99, published by the American Optometric Association online.

According to Cooper et al., myopia is classified in three groups: pathologic (usually before age six), school age (between the ages of 6 and 18) and adult onset. Myopia progression is greatest in young children. Treatments include spectacle correction (bifocals and multifocal lenses), contact lenses (single vision contact lenses, orthokeratology, multifocal soft contact lenses), atropine and pirenzepine. Generally speaking, bifocals and progressive lenses have not been very effective in slowing the progression of myopia in children. While orthokeratology and soft contact lenses have recently shown some success, the progression of myopia has been most effectively slowed by topical atropine, which is known as an anticholinergic/mydriatic agent. See also Chua et al., "Atropine for the Treatment of Childhood Myopia", *Ophthalmology* 2006; 113; 2285-2291, American Academy of Ophthalmology, published by Elsevier Inc.; Chia et al., "Atropine for the Treatment of Childhood Myopia: Safety and Efficacy of 0.5%, 0.1% and 0.01% Doses (Atropine for the Treatment of Myopia 2), *Ophthalmology* 2012; 119; 347-354, American Academy of Ophthalmology, published by Elsevier Inc.; and Fang et al., "Prescription of atropine eye drops among children diagnosed with myopia in Taiwan from 2000 to 2007: a nationwide study", *Eye* (2013), 1-7, Macmillan Publishers.

Atropine was used as early as the nineteenth century for slowing myopia progression, but fell into disfavor after the turn of the twentieth century. However, interest revived in using topical atropine to slow myopia progression in the 1960's and has continued since that time. Progressively lower concentrations have been tested and found effective. In the ATOM2 studies detailed by Chia et al. referenced above, the mean myopia progression at 2 years was as follows: for 0.5% atropine, 0.15 D/year; for 0.1% atropine, 0.19 D/year; and for 0.01% atropine, 0.24 D/year. Although no serious adverse events were reported, there appears to be a bias against atropine in the art because of atropine's possible side effects.

The possible side effects of atropine can include dry mouth, photophobia, blurred vision, urinary hesitancy and retention, decreased sweating, drowsiness, dizziness, restlessness, irritability, disorientation, hallucinations, tachycardia and cardiac arrhythmias, nausea, constipation, and severe allergic reactions, which often limit its clinical use, and even topical anticholinergics can cause the same unwanted side effects. Glycopyrrolate is among the quaternary ammonium anticholinergics, which have reduced CNS-related side effects as they cannot cross the blood-brain barrier; however, because glycopyrrolate is eliminated mainly as unchanged drug or active metabolite in the urine, its administration is problematic in young or elderly patients and especially in uraemic patients.

Pirenzepine, a M1-selective antagonist previously used to treat gastric ulcers, does not have mydriatic properties, but has been found effective as a 2% ophthalmic gel in slowing the progression of myopia in a group of school-aged children, although not as successfully as topical atropine. Moreover, pirenzepine is not approved by the FDA.

In view of the foregoing, it is apparent that there is need for an alternative pharmacological approach to the treatment of myopia, particularly for slowing the progression of myopia, especially severe myopia, in school-age children or for treating myopia in adults which does not utilize topical atropine or pirenzepine.

Previously, we provided a method for slowing progression of myopia in a child aged from about 6 to about 18 who is afflicted with same, said method comprising administering to the eyes of said child, at least once per week for a time period of at least one year, an effective amount of a compound selected from the group consisting of:
(i) (±) 3-(2-cyclopentyl-2-phenyl-2-hydroxyacetoxy)-1-(carboxymethyl)-1-methylpyrrolidinium inner salt;
(ii) (2R) 3-(2-cyclopentyl-2-phenyl-2-hydroxyacetoxy)-1-(carboxymethyl)-1-methylpyrrolidinium inner salt;
(iii) (2R, 1'R, 3'R) 3-(2-cyclopentyl-2-phenyl-2-hydroxyacetoxy)-1-(carboxymethyl)-1-methylpyrrolidinium inner salt;
(iv) (2R, 1'S, 3'R) 3-(2-cyclopentyl-2-phenyl-2-hydroxyacetoxy)-1-(carboxymethyl)-1-methylpyrrolidinium inner salt;
(v) (2R, 1'R, 3'S) 3-(2-cyclopentyl-2-phenyl-2-hydroxyacetoxy)-1-(carboxymethyl)-1-methylpyrrolidinium inner salt; and
(vi) (2R, 1'S, 3'S) 3-(2-cyclopentyl-2-phenyl-2-hydroxyacetoxy)-1-(carboxymethyl)-1-methylpyrrolidinium inner salt;
as well as compositions for use in that method and the use itself.

In another aspect, we also previously provided a method for treating myopia in a subject afflicted with same, said method comprising administering to the eyes of said subject, at least once per week, an effective amount of at least one compound selected from the group consisting of:

(i) (±) 3-(2-cyclopentyl-2-phenyl-2-hydroxyacetoxy)-1-(carboxymethyl)-1-methylpyrrolidinium inner salt;

(ii) (2R) 3-(2-cyclopentyl-2-phenyl-2-hydroxyacetoxy)-1-(carboxymethyl)-1-methylpyrrolidinium inner salt;

(iii) (2R, 1'R, 3'R) 3-(2-cyclopentyl-2-phenyl-2-hydroxyacetoxy)-1-(carboxymethyl)-1-methylpyrrolidinium inner salt;

(iv) (2R, 1'S, 3'R) 3-(2-cyclopentyl-2-phenyl-2-hydroxyacetoxy)-1-(carboxymethyl)-1-methylpyrrolidinium inner salt;

(v) (2R, 1'R, 3'S) 3-(2-cyclopentyl-2-phenyl-2-hydroxyacetoxy)-1-(carboxymethyl)-1-methylpyrrolidinium inner salt; and (vi) (2R, 1'S, 3'S) 3-(2-cyclopentyl-2-phenyl-2-hydroxyacetoxy)-1-(carboxymethyl)-1-methylpyrrolidinium inner salt;

as well as compositions for use in that method and the use itself.

Said methods, compositions and use, however, were not published at the time of the filing date of the priority application for the present PCT application.

SUMMARY

Provided herein is use of an effective amount of at least one compound selected from the group consisting of:

(vii) (2R, 3'R) 3-(2-cyclopentyl-2-phenyl-2-hydroxyacetoxy)-1-(carboxymethyl)-1-methylpyrrolidinium inner salt;

(viii) (2R, 3'S) 3-(2-cyclopentyl-2-phenyl-2-hydroxyacetoxy)-1-(carboxymethyl)-1-methylpyrrolidinium inner salt;

(ix) (2R, 1'R) 3-(2-cyclopentyl-2-phenyl-2-hydroxyacetoxy)-1-(carboxymethyl)-1-methylpyrrolidinium inner salt; and (x) (2R, 1'S) 3-(2-cyclopentyl-2-phenyl-2-hydroxyacetoxy)-1-(carboxymethyl)-1-methylpyrrolidinium inner salt;

in the preparation of an ophthalmic medicament composition comprising said at least one compound, in slowing the progression of myopia in a child aged from about 6 to about 18 who is afflicted therewith by topically administering said composition to the eyes of said child, at least once per week for a time period of at least one year.

In a second aspect, there is provided herein use of an effective amount of at least one compound selected from the group consisting of:

(vii) (2R, 3'R) 3-(2-cyclopentyl-2-phenyl-2-hydroxyacetoxy)-1-(carboxymethyl)-1-methylpyrrolidinium inner salt;

(viii) (2R, 3'S) 3-(2-cyclopentyl-2-phenyl-2-hydroxyacetoxy)-1-(carboxymethyl)-1-methylpyrrolidinium inner salt;

(ix) (2R, 1'R) 3-(2-cyclopentyl-2-phenyl-2-hydroxyacetoxy)-1-(carboxymethyl)-1-methylpyrrolidinium inner salt; and (x) (2R, 1'S) 3-(2-cyclopentyl-2-phenyl-2-hydroxyacetoxy)-1-(carboxymethyl)-1-methylpyrrolidinium inner salt;

in the preparation of an ophthalmic medicament composition comprising said at least one compound, in treating myopia in a subject afflicted therewith by topically administering said composition to the eyes of said subject at least once per week.

In a third aspect, there is provided herein a method for slowing progression of myopia in a child aged from about 6 to about 18 who is afflicted therewith, said method comprising topically administering to the eyes of said child, at least once per week for a time period of at least one year, an effective amount of at least one compound selected from the group consisting of:

(vii) (2R, 3'R) 3-(2-cyclopentyl-2-phenyl-2-hydroxyacetoxy)-1-(carboxymethyl)-1-methylpyrrolidinium inner salt;

(viii) (2R, 3'S) 3-(2-cyclopentyl-2-phenyl-2-hydroxyacetoxy)-1-(carboxymethyl)-1-methylpyrrolidinium inner salt;

(ix) (2R, 1'R) 3-(2-cyclopentyl-2-phenyl-2-hydroxyacetoxy)-1-(carboxymethyl)-1-methylpyrrolidinium inner salt; and (x) (2R, 1'S) 3-(2-cyclopentyl-2-phenyl-2-hydroxyacetoxy)-1-(carboxymethyl)-1-methylpyrrolidinium inner salt;

said at least one compound being optionally administered in the form of an ophthalmic composition comprising said effective amount of said compound and a non-toxic, ophthalmically acceptable carrier.

In a fourth aspect, there is provided herein a method for treating myopia in a subject afflicted therewith, said method comprising topically administering to the eyes of said subject, at least once per week, an effective amount of at least one compound selected from the group consisting of:

(vii) (2R, 3'R) 3-(2-cyclopentyl-2-phenyl-2-hydroxyacetoxy)-1-(carboxymethyl)-1-methylpyrrolidinium inner salt;

(viii) (2R, 3'S) 3-(2-cyclopentyl-2-phenyl-2-hydroxyacetoxy)-1-(carboxymethyl)-1-methylpyrrolidinium inner salt;

(ix) (2R, 1'R) 3-(2-cyclopentyl-2-phenyl-2-hydroxyacetoxy)-1-(carboxymethyl)-1-methylpyrrolidinium inner salt; and (x) (2R, 1'S) 3-(2-cyclopentyl-2-phenyl-2-hydroxyacetoxy)-1-(carboxymethyl)-1-methylpyrrolidinium inner salt;

said at least one compound being optionally administered in the form of an ophthalmic composition comprising said effective amount of said compound and a non-toxic, ophthalmically acceptable carrier In a fifth aspect, there is provided herein an ophthalmic composition comprising (a) an effective amount of at least one compound selected from the group consisting of:

(vii) (2R, 3'R) 3-(2-cyclopentyl-2-phenyl-2-hydroxyacetoxy)-1-(carboxymethyl)-1-methylpyrrolidinium inner salt;

(viii) (2R, 3'S) 3-(2-cyclopentyl-2-phenyl-2-hydroxyacetoxy)-1-(carboxymethyl)-1-methylpyrrolidinium inner salt;

(ix) (2R, 1'R) 3-(2-cyclopentyl-2-phenyl-2-hydroxyacetoxy)-1-(carboxymethyl)-1-methylpyrrolidinium inner salt; and (x) (2R, 1'S) 3-(2-cyclopentyl-2-phenyl-2-hydroxyacetoxy)-1-(carboxymethyl)-1-methylpyrrolidinium inner salt;

and (b) a non-toxic ophthalmically acceptable carrier, for use in the treatment of myopia, wherein said composition is to be topically administered to the eyes of a subject afflicted with myopia at least once per week, particularly when the composition is to be administered at least once per week for a time period of at least one year, to a child aged from about 6 to about 18 afflicted with myopia to slow its progression

DETAILED DESCRIPTION

In preferred aspects of the uses, methods of treatment and compositions for use specified in the SUMMARY above, the following embodiments are contemplated, separately and in combination:

(1) the composition is administered once or twice per day, for from one to seven days per week;

(2) the administration is carried out for a time period of at least two years;

(3) the at least one compound in the composition is (2R, 3'R) 3-(2-cyclopentyl-2-phenyl-2-hydroxyacetoxy)-1-(carboxymethyl)-1-methylpyrrolidinium inner salt;

(4) the compound is present in the composition in an amount of from about 0.2% w/v to about 1% w/v.

The compounds (i) through (x) above have been among compounds previously described as soft anticholinergic zwitterions which are products of the hydrolysis of the corresponding soft anticholinergic esters. See, for example, Bodor Published United States Application No. US2012/0141401A1, published Jun. 7, 2013; Bodor U.S. Pat. No. 8,071,639; Bodor U.S. Pat. No. 8,147,809 and other U.S. and foreign counterparts thereof. See also Wu et al., "Pharmacokinetic and Pharmacodynamic Evaluations of the Zwitterionic Metabolite of a New Series of N-Substituted Soft Anticholinergics", *Pharmaceutical Research*, Vol. 22, No. 12, pp. 2035-2044, 12 Dec. 2005 (available online 26 Sep. 2005), Kluwer Academic, Plenum Publishers, U.S. The above-mentioned patent documents describe the synthesis and resolution of the compounds and also contain pharmacological test data.

According to the patents and applications describing the soft anticholinergic zwitterions, the compounds of this type are much less active anticholinergics than the corresponding esters, by about an order of magnitude, yet are nevertheless useful as anticholinergics; among their anticholinergic uses, the compounds of this type are taught to be useful in treating overactive bladder, COPD and other respiratory conditions, and also in inducing short-acting mydriasis and thus can be used to dilate the pupils of the eyes in vision testing.

Mydriatic studies in rabbit eyes have been previously described for compound (ii) above, compared to glycopyrrolate, tropicamide and two soft anticholinergic esters. Compound (ii) produced local mydriatic activity after topical administration but only with a short duration of action. The racemic form, compound (i) above, showed even lower potency.

Furthermore, compound (ii) has been found to not cause any observable irritation reactions, such as eye-closing, lacrimation, or mucous discharge; and unlike conventional anticholinergics, it did not cause pupil dilation in the contralateral, untreated eye, indicating not only low topical and systemic side effects, but also rapid elimination from the systemic circulation.

Compound (i) above has the following structural formula:

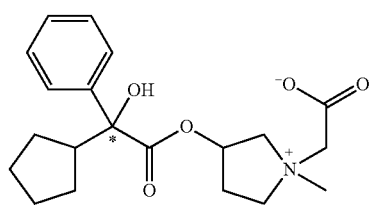

(Ia-i)

wherein the asterisk indicates that the compound is unresolved at the 2-position, that is, that the compound is the racemic mixture of 2R and 2S stereoisomers. The compound is also unresolved at the 1'- and 3'-positions.

Compound (ii) above can be represented by the following structural formula:

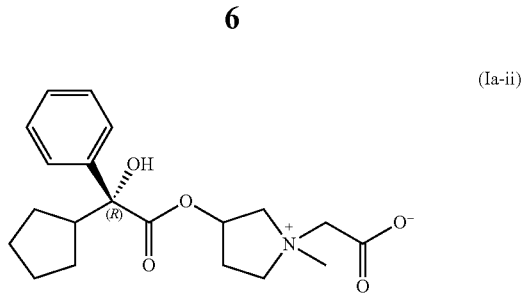

(Ia-ii)

This compound has the 2R configuration, but is unresolved at the 1'- and 3'-positions.

Compounds (iii) through (x) have the structural formula:

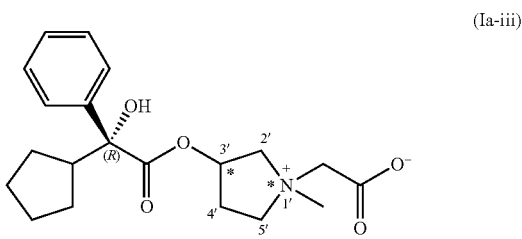

(Ia-iii)

wherein the asterisks indicate that the compounds are resolved at one or both of the 1' and 3' positions. The compound thus has one of the following configurations: (2R, 1'R, 3'R), (2R, 1'S, 3'R), (2R, 1'R, 3'S), (2R, 1'S, 3'S), (2R, 3'R), (2R, 3'S), (2R, 1'R) and (2R, 1'S).

Throughout this specification, the following definitions, general statements and illustrations are applicable:

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process or method, the term "comprising" means that the process or method includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or method or composition; for example, steps or features or components which would significantly interfere with the desired properties of the compounds or compositions described herein, i.e., the process or composition is limited to the specified steps or materials and those which do not materially affect its basic and novel characteristics. The basic and novel features herein are the provision of compounds (i) through (x) as defined above for use in a method of slowing the progression of myopia in children, or in a method for treating myopia in a subject afflicted with that condition.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not in the "exclusive" sense of "either/or."

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001).

As used herein, "treating" means reducing or alleviating symptoms in the individual to which a compound or composition as described herein has been administered, as compared to the symptoms of an individual not being treated as described herein. The expression "slowing the progression of" means "hindering or inhibiting the development of". A practitioner will appreciate that the compounds, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the frequency of administration.

The methods described herein are intended for use with any subject/patient that may experience their benefits. Thus, in accordance herewith, the terms "subjects" as well as "patients," "individuals" and "warm-blooded animals" include humans as well as non-human subjects, particularly domesticated animals, particularly dogs, cats, horses and cows, as well as other farm animals, zoo animals and/or endangered species. The expressions "child" or "children" refer to humans aged from about 6 to about 18.

To treat myopia, compounds (vii) through (x), like compounds (i) through (vi), are conveniently administered topically to the eyes in the form of an ophthalmic composition comprising an effective amount of the selected compound(s) and a non-toxic, ophthalmically acceptable carrier therefor. Ophthalmically acceptable carriers, or diluents, are well-known in the art. The compounds are both soluble and stable in water. Consequently, the carrier, e.g., non-active ingredient, can be just (sterile) water with the pH adjusted to where the active pharmaceutical agent is very soluble. It is preferred that the pH be at or near 7. Alternatively and preferably, the non-active carrier agent can be physiological saline with the pH adjusted appropriately. Eye drops and eye gels are particularly suited to ophthalmic administration.

The amount of compound (vii) through (x) effective to treat myopia or to slow the progression of myopia in a child is generally a mydriatically effective amount, that is, like the amount of compound (i) to (vi), it is an amount sufficient to elicit a mydriatic response, i.e., an amount sufficient to induce mydriasis (dilate the pupils) in the treated eyes. Compound (i) provokes a weaker response than the other compounds and would typically be used at twice the amount of one of compounds (ii) through (vi). For compounds (vii) through (x), administration can conveniently be by way of an ophthalmic composition preferably containing from about 0.2% (w/v), especially from about 0.25% (w/v) to about 1% (w/v), most especially from about 0.5% (w/v) to about 1% (w/v) of the selected compound, and an ophthalmically acceptable carrier. However, the compounds employed in the methods and uses herein are ideal "hard" drugs because they are not further metabolized and show no toxicity when administered to the eyes. Consequently, these compounds can be administered at even higher concentrations than suggested above, particularly from about 1% (w/v) to about 2% (w/v) or more, without provoking deleterious side effects.

In carrying out the methods and uses herein, the selected compound is administered from as frequently as once or twice per day, for from two to seven days per week, to as infrequently as once a week. In children, treatment is continued for at least one year, more often for at least two years, or for a greater number of years until the myopia has stabilized (in the late teens or early twenties). Thus, to slow the progression of myopia, children with myopia may be treated for as long as ten years or more. While there is typically regression after discontinuance of drug administration, there is overall improvement in comparison to myopic children who have not been treated with an anticholinergic agent during their school years. Adult treatment is typically once daily. Dosages and frequency of administration may be adjusted by the ophthalmologist depending upon a particular patient's response. In school-aged children, again depending upon the child's response, treatment may even be limited to weekends. In particular cases, administration of one of the compounds may be accompanied by the use of glasses or contact lenses.

EXPERIMENTAL DETAILS

Objectives

The mydriatic activity of Compound (ii), also referred to as (2R)SGA, was investigated to evaluate its pharmacological effect and character in human eyes for possible myopia treatment in children.

Methods

The mydriatic effects of the representative zwitterion (2R)SGA and tropicamide were compared after topical administration in the same two human subjects (age 40~50). A 100 μL aliquot of a 1% (w/v) compound solution was administered in each eye of each subject. Experiments were carried out in a light and temperature-controlled room. At appropriate time intervals, the pupil diameters of each eye of each subject were recorded. Difference in pupil diameters between each time-point and zero time-point were calculated and reported as mydriatic response [(treated-control)/control in %]. The area under the mydriatic response-time curve ($AUC^{\mathit{eff}}$) was calculated by the trapezoidal rule, and was used to compare the activity and duration of the tested compounds. A control study was also performed using normal saline (100 μL) in each eye of each subject, and has been confirmed as "no pupil dilation".

Results and Discussion

After topical administration, the potency and duration of the representative zwitterion (2R)SGA was compared to that of tropicamide, the most frequently used mydriatic agent. Following topical administration of 100 μL in each eye of each of two human subjects, the pupil size was measured periodically, and the maximum mydriatic effect (Emax, % change in pupil size) and area under the mydriatic response-time curves ($AUC^{\mathit{eff}}_{0-168h}$) were determined and compared (Table 1). The zwitterionic (2R)SGA produced a good local mydriatic activity that was similar to tropicamide. Although the onset of activity was slower [3 hours for (2R)SGA versus 0.5 hours for tropicamide], the duration of action was much longer than in the case of tropicamide. The recovery times, that is, the time periods needed for the size of pupil in the treated eye to recover to within less than 1 mm of the control, of (2R)SGA were approximately 120 hours and 36 hours for subject 1 and subject 2, respectively, compared to tropicamide (8 hours and 3.5 hours for subject 1 and subject 2, respectively). In human eyes, (2R)SGA [Compound (ii)] did not cause any uncomfortable sensations. Adding these results to the previous reports in rabbit studies on (2R)SGA (no pupil dilation in the contralateral untreated eye when administered in one eye; and rapid elimination from systemic circulation), the safe characteristics of the representative Compound (ii) has been confirmed. In addition, lower doses (for example, 0.5% w/v or less) are suggested as particularly advantageous for slowing the progression of myopia in children.

TABLE 1

Pharmacodynamic Parameters after 1%, 0.1 ml administration in human eyes.

| Parameter | (2R)SGA Mean | (2R)SGA SD | Tropicamide Mean | Tropicamide SD |
|---|---|---|---|---|
| Emax, % | 125.0 | 16.7 | 137.5 | 8.3 |
| Time to Emax, hr | 3 | | 0.5 | |
| $AUC_{0-168}$ (%)xhr | 7436.5 | 4138.2 | 600.0 | 146.4 |

TABLE 2

Mydriatic study of (2R)SGA & Tropicamide (1%) in human eyes
Compound in solution, 0.1 ml, was administered in both eyes.
A) (2R)SGA 0.2% solution, 0.1 ml applied - No pupil dilation was found in 2 hr.
B) 1%, 0.1 ml was administered - Mydriatic activity was observed and recorded.
C) 1% Tropicamide (Bausch & Lomb) 0.1 ml was also administered for comparison.

Results-
(2R)SGA (1%, 0.1 ml)

Subject 1 Right eye

| Time, hr | 0 | 0.25 | 0.5 | 0.75 | 1 | 1.5 | 2 | 3 | 4 | 5 | 6 |
|---|---|---|---|---|---|---|---|---|---|---|---|
| Pupil Size, mm | 3 | 3.5 | 4 | 5.5 | 6.25 | 6.25 | 6.5 | 7 | 6.75 | 6.5 | 6.5 |
| -Control | 0 | 0.5 | 1 | 2.5 | 3.25 | 3.25 | 3.5 | 4 | 3.75 | 3.5 | 3.5 |
| % dilation | 0 | 17 | 33 | 83 | 108 | 108 | 117 | 133 | 125 | 117 | 117 |
| Time, hr | 7 | 8 | 12 | 24 | 36 | 48 | 72 | 96 | 120 | 144 | 168 |
| Pupil Size, mm | 6 | 6 | 6 | 6 | 6 | 5.75 | 5.5 | 5 | 4.5 | 4 | 3.5 |
| -Control | 3 | 3 | 3 | 3 | 3 | 2.75 | 2.5 | 2 | 1.5 | 1 | 0.5 |
| % dilation | 100 | 100 | 100 | 100 | 100 | 92 | 83 | 67 | 50 | 33 | 17 |

Left Eye

| Time, hr | 0 | 0.25 | 0.5 | 0.75 | 1 | 1.5 | 2 | 3 | 4 | 5 | 6 |
|---|---|---|---|---|---|---|---|---|---|---|---|
| Pupil Size, mm | 3 | 3.5 | 4 | 5.5 | 6.25 | 6.25 | 6.5 | 7 | 6.75 | 6.5 | 6.5 |
| -Control | 0 | 0.5 | 1 | 2.5 | 3.25 | 3.25 | 3.5 | 4 | 3.75 | 3.5 | 3.5 |
| % dilation | 0 | 17 | 33 | 83 | 108 | 108 | 117 | 133 | 125 | 117 | 117 |
| Time, hr | 7 | 8 | 12 | 24 | 36 | 48 | 72 | 96 | 120 | 144 | 168 |
| Pupil Size, mm | 6 | 6 | 6 | 6 | 6 | 5.5 | 5 | 4.5 | 4 | 3.75 | 3.5 |
| -Control | 3 | 3 | 3 | 3 | 3 | 2.5 | 2 | 1.5 | 1 | 0.75 | 0.5 |
| % dilation | 100 | 100 | 100 | 100 | 100 | 83 | 67 | 50 | 33 | 25 | 17 |

Subject 2 Right eye

| Time, hr | 0 | 0.25 | 0.5 | 0.75 | 1 | 1.5 | 2 | 3 | 4 | 5 | 6 |
|---|---|---|---|---|---|---|---|---|---|---|---|
| Pupil Size, mm | 3 | 4 | 6 | 6 | 6 | 6 | 6 | 6 | 6 | 6 | 6 |
| -Control | 0 | 1 | 3 | 3 | 3 | 3 | 3 | 3 | 3 | 3 | 3 |
| % dilation | 0 | 33 | 100 | 100 | 100 | 100 | 100 | 100 | 100 | 100 | 100 |
| Time, hr | 7 | 8 | 12 | 24 | 36 | 48 | 72 | 96 | 120 | 144 | 168 |
| Pupil Size, mm | 6 | 6 | 5.5 | 4.5 | 3.5 | 3.5 | 3.5 | 3 | 3 | 3 | 3 |
| -Control | 3 | 3 | 2.5 | 1.5 | 0.5 | 0.5 | 0.5 | 0 | 0 | 0 | 0 |
| % dilation | 100 | 100 | 83 | 50 | 17 | 17 | 17 | 0 | 0 | 0 | 0 |

TABLE 2-continued

Mydriatic study of (2R)SGA & Tropicamide (1%) in human eyes
Compound in solution, 0.1 ml, was administered in both eyes.
A) (2R)SGA 0.2% solution, 0.1 ml applied - No pupil dilation was found in 2 hr.
B) 1%, 0.1 ml was administered - Mydriatic activity was observed and recorded.
C) 1% Tropicamide (Bausch & Lomb) 0.1 ml was also administered for comparison.

Left Eye

| Time, hr | 0 | 0.25 | 0.5 | 0.75 | 1 | 1.5 | 2 | 3 | 4 | 5 | 6 |
|---|---|---|---|---|---|---|---|---|---|---|---|
| Pupil Size, mm | 3 | 4 | 6.5 | 6.5 | 6.5 | 6.5 | 6.5 | 7 | 7 | 6.75 | 6.75 |
| -Control | 0 | 1 | 3.5 | 3.5 | 3.5 | 3.5 | 3.5 | 4 | 4 | 3.75 | 3.75 |
| % dilation | 0 | 33 | 117 | 117 | 117 | 117 | 117 | 133 | 133 | 125 | 125 |
|  | 7 | 8 | 12 | 24 | 36 | 48 | 72 | 96 | 120 | 144 | 168 |
|  | 6.75 | 6.75 | 6.5 | 5.5 | 4.5 | 4 | 3.5 | 3 | 3 | 3 | 3 |
|  | 3.75 | 3.75 | 3.5 | 2.5 | 1.5 | 1 | 0.5 | 0 | 0 | 0 | 0 |
|  | 125 | 125 | 117 | 83 | 50 | 33 | 17 | 0 | 0 | 0 | 0 |

Tropicamide (1%, 0.1 ml)

Subject 1
Right eye

| Time, hr | 0 | 0.25 | 0.5 | 0.75 | 1 | 1.5 | 2 | 4 | 6 | 8 | 10 |
|---|---|---|---|---|---|---|---|---|---|---|---|
| Pupil Size, mm | 3 | 6.5 | 6.5 | 7 | 7 | 7 | 6.5 | 6 | 5 | 4 | 3 |
| -Control | 0 | 3.5 | 3.5 | 4 | 4 | 4 | 3.5 | 3 | 2 | 1 | 0 |
| % dilation | 0 | 117 | 117 | 133 | 133 | 133 | 117 | 100 | 67 | 33 | 0 |

Left Eye

| Time, hr | 0 | 0.25 | 0.5 | 0.75 | 1 | 1.5 | 2 | 3 | 4 | 5 | 6 |
|---|---|---|---|---|---|---|---|---|---|---|---|
| Pupil Size, mm | 3 | 6 | 6.5 | 7 | 7 | 7 | 6.5 | 6 | 4.5 | 3.5 | 3 |
| -Control | 0 | 3 | 3.5 | 4 | 4 | 4 | 3.5 | 3 | 1.5 | 0.5 | 0 |
| % dilation | 0 | 100 | 117 | 133 | 133 | 133 | 117 | 100 | 50 | 17 | 0 |

Subject 2
Right eye

| Time, hr | 0 | 0.25 | 0.5 | 0.75 | 1 | 1.5 | 2 | 3 | 4 | 5 | 6 |
|---|---|---|---|---|---|---|---|---|---|---|---|
| Pupil Size, mm | 3 | 5.5 | 7 | 7 | 7 | 7 | 6 | 4.5 | 3 | 3 | 3 |
| -Control | 0 | 2.5 | 4 | 4 | 4 | 4 | 3 | 1.5 | 0 | 0 | 0 |
| % dilation | 0 | 83 | 133 | 133 | 133 | 133 | 100 | 50 | 0 | 0 | 0 |

Left Eye

| Time, hr | 0 | 0.25 | 0.5 | 0.75 | 1 | 1.5 | 2 | 3 | 4 | 5 | 6 |
|---|---|---|---|---|---|---|---|---|---|---|---|
| Pupil Size, mm | 3 | 6 | 7.5 | 7.5 | 7.5 | 7.5 | 6.25 | 5 | 3.5 | 3 | 3 |
| -Control | 0 | 3 | 4.5 | 4.5 | 4.5 | 4.5 | 3.25 | 2 | 0.5 | 0 | 0 |
| % dilation | 0 | 100 | 150 | 150 | 150 | 150 | 108 | 67 | 17 | 0 | 0 |

TABLE 3

% Change in pupil size after 1% administration
Subjects 1 & 2

(2R)SGA (1%, 0.1 ml)

| Hr | 0 | 0.25 | 0.5 | 0.75 | 1 | 1.5 | 2 | 3 | 4 | 5 | 6 | 7 |
|---|---|---|---|---|---|---|---|---|---|---|---|---|
| #1-R | 0.0 | 16.7 | 33.3 | 83.3 | 108.3 | 108.3 | 116.7 | 133.3 | 125.0 | 116.7 | 116.7 | 100.0 |
| #1-L | 0.0 | 16.7 | 33.3 | 83.3 | 108.3 | 108.3 | 116.7 | 133.3 | 125.0 | 116.7 | 116.7 | 100.0 |
| #2-R | 0.0 | 33.3 | 100.0 | 100.0 | 100.0 | 100.0 | 100.0 | 100.0 | 100.0 | 100.0 | 100.0 | 100.0 |
| #2-L | 0.0 | 33.3 | 116.7 | 116.7 | 116.7 | 116.7 | 116.7 | 133.3 | 133.3 | 125.0 | 125.0 | 125.0 |
| Mean | 0.0 | 25.0 | 70.8 | 95.8 | 108.3 | 108.3 | 112.5 | 125.0 | 120.8 | 114.6 | 114.6 | 106.3 |
| SD | 0.0 | 9.6 | 43.8 | 16.0 | 6.8 | 6.8 | 8.3 | 16.7 | 14.4 | 10.5 | 10.5 | 12.5 |

| Hr | 8 | 12 | 24 | 36 | 48 | 72 | 96 | 120 | 144 | 168 | $AUC_{0-168}$ |
|---|---|---|---|---|---|---|---|---|---|---|---|
| #1-R | 100.0 | 100.0 | 100.0 | 100.0 | 91.7 | 83.3 | 66.7 | 50.0 | 33.3 | 16.7 | 11707.3 |
| #1-L | 100.0 | 100.0 | 100.0 | 100.0 | 83.3 | 66.7 | 50.0 | 33.3 | 25.0 | 16.7 | 10157.3 |
| #2-R | 100.0 | 83.3 | 50.0 | 16.7 | 16.7 | 16.7 | 0.0 | 0.0 | 0.0 | 0.0 | 3137.5 |
| #2-L | 125.0 | 116.7 | 83.3 | 50.0 | 33.3 | 16.7 | 0.0 | 0.0 | 0.0 | 0.0 | 4743.8 |
| Mean | 106.3 | 100.0 | 83.3 | 66.7 | 56.3 | 45.8 | 29.2 | 20.8 | 14.6 | 8.3 | 7436.5 |
| SD | 12.5 | 13.6 | 23.6 | 40.8 | 36.9 | 34.4 | 34.4 | 25.0 | 17.2 | 9.6 | 4138.2 |

TABLE 3-continued

% Change in pupil size after 1% administration
Subjects 1 & 2

Tropicamide (1%, 0.1 ml)

| | \multicolumn{11}{c}{Hr} | |
| | 0 | 0.25 | 0.5 | 0.75 | 1 | 1.5 | 2 | 4 | 6 | 8 | 10 | $AUC_{0-168}$ |
|---|---|---|---|---|---|---|---|---|---|---|---|---|
| #1-R | 0.0 | 116.7 | 116.7 | 133.3 | 133.3 | 133.3 | 116.7 | 100.0 | 66.7 | 33.3 | 0.0 | 754.2 |
| #1-L | 0.0 | 100.0 | 116.7 | 133.3 | 133.3 | 133.3 | 116.7 | 100.0 | 50.0 | 16.7 | 0.0 | 683.3 |
| #2-R | 0.0 | 83.3 | 133.3 | 133.3 | 133.3 | 133.3 | 100.0 | 50.0 | 0.0 | 0.0 | 0.0 | 429.2 |
| #2-L | 0.0 | 100.0 | 150.0 | 150.0 | 150.0 | 150.0 | 108.3 | 66.7 | 16.7 | 0.0 | 0.0 | 533.3 |
| Mean | 0.0 | 100.0 | 129.2 | 137.5 | 137.5 | 137.5 | 110.4 | 79.2 | 33.3 | 12.5 | 0.0 | 600.0 |
| SD | 0.0 | 13.6 | 16.0 | 8.3 | 8.3 | 8.3 | 8.0 | 25.0 | 30.4 | 16.0 | 0.0 | 146.4 |

| | (2R)SGA | | Tropicamide | |
|---|---|---|---|---|
| | Mean | SD | Mean | SD |
| Emax, % | 125.0 | 16.7 | 137.5 | 8.3 |
| Time to Emax, hr | 3 | | 0.5~0.75 | |
| AUC | 7436.5 | 4138.2 | 600.0 | 146.4 |

TABLE 4

% Change in pupil size after 1% administration, AUC(0-168 hours)
Subjects 1 & 2

| | AUC(0-168 hr) |
|---|---|
| \multicolumn{2}{c}{(2R)SGA (1%, 0.1 ml)} |
| #1-R | 11707.3 |
| #1-L | 10157.3 |
| #2-R | 3137.5 |
| #2-L | 4743.8 |
| Mean | 7436.5 |
| SD | 4138.2 |
| \multicolumn{2}{c}{Tropicamide (1%, 0.1 ml)} |
| #1-R | 754.2 |
| #1-L | 683.3 |
| #2-R | 429.2 |
| #2-L | 533.3 |
| Mean | 600 |
| SD | 146.4 |

Further Discussion

It is surprising to find such high and prolonged mydriatic activity for the zwitterion when applied to the eye because it is very weak in terms of intrinsic anticholinergic activity as characterized by pA2 (as reported earlier). In addition, when administered intravenously, the zwitterion is eliminated very quickly, yet it has a long activity when instilled into the eye, suggesting "kinetic selectivity," strong and prolonged binding to the receptors in the eye, yet it is eliminated quickly with no side effects (no activity in untreated contralateral eye). Thus, surprisingly, an "inactive metabolite" (decrease of at least 10 fold in pA2 compared to corresponding soft esters) has comparable or higher activity than the potent soft or hard analogue (glycopyrrolate) in the eye. The inactive metabolite is actually an ideal "hard drug" because it is not further metabolized.

While most anticholinergics used are positively charged (either quaternary salts or highly basic tertiary amines which of course are protonated), the zwitterions are neutral, just like tropicamide, but the activity is surprisingly much longer. It also appears that the corresponding soft esters do not possess the same properties, although they are designed to be metabolized to the active zwitterions. But it appears that this transformation does not take place predominantly in the eye but rather systemically, or possibly the part in the eye does not release it at the site needed. At any rate, the high mydriatic activity of the zwitterions when applied in the eye is truly surprising.

Clinical Study Design

A clinical study is proposed to assess the efficacy of ophthalmic formulations of one or more selected zwitterions [such as Compound (ii) or (vii)] for their ability to slow the progression of myopia in children. Two concentrations of each selected zwitterion would be tested, either 1.0% or 0.5%. Patients, as described below, would receive two drops of the test formulation in each eye, every two days. The treatment would continue for 2 years, then the patients would be followed for another 2 years to assess the effect on myopia progression. A starting baseline would be obtained, and assessments would be made during the treatment at 4, 8, 12, 16, 20, and 24 months. During the follow-up period after treatment has been terminated, assessments would be at 6-month intervals.

In following previously designed clinical studies to assess myopia therapeutics, patients would be enrolled in Singapore who had been diagnosed with myopic refraction of at least 2.0 D in both eyes (diagnosed as following the International Classification of Diseases, Ninth Clinical Modification (ICD-9-CM) ICD 367) and who had the following characteristics: documented myopic progression of at least 0.5 D in the past year; are between the ages of 6 and 12; did not exhibit one of the following ocular pathologies: anterior or pan-uveitis, accommodative esotropia, malignant glaucoma, or inflammatory glaucoma; did not have any systemic ill health; had not exhibited any allergic tendencies to anticholinergics; and had not been previously treated for myopia. The goal would be to have at least 100 patients allocated to each of the two treatment groups for each selected zwitterion.

The inclusion of an active or inactive control is not necessary as a number of previous studies have been conducted controlling for both treated and untreated conditions, providing significant data with which to compare the results of the proposed study.

The proposed study would be conducted according to the tenets of the Declaration of Helsinki and would seek approval from the Singapore Eye Research Institute Review Board.

The following Examples illustrate ophthalmic formulations suitable for administering the zwitterions to treat myopia or to slow the progression of myopia in school-aged children. These formulations are made by well-known procedures.

In these Examples, percentages are by weight unless otherwise indicated.

Example 1

| EYE DROPS | |
|---|---|
| Selected zwitterion, e.g. Compound (ii) or (vii) | 0.25%, 0.50%, 0.75% or 1.0% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

Example 2

| EYE DROPS | |
|---|---|
| Selected zwitterion, e.g. Compound (iii) or (vii) | 0.25%, 0.50%, 0.75%, or 1% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

Example 3

| EYE DROPS | |
|---|---|
| Selected zwitterion, e.g. Compound (ii) or (vii) | 0.25%, 0.50%, 0.75% or 1.0% w/v |
| Povidone | 0.6% w/v |
| Benzalkonium chloride | 0.02% w/v |
| Sodium edetate U.S.P. | 0.10% w/v |
| Glycerin U.S.P. | 2.5% w/v |
| Tyloxapol U.S.P. | 3.0% w/v |
| Sodium chloride | 0.3% w/v |
| Sodium γ-aminobutyrate | 1.0% w/v |
| Sterile distilled water | q.s. 100 volumes |
| NaOH or HCl | to pH 5.0-5.5 |

While this description has been couched in terms of various preferred or exemplary embodiments, the skilled artisan will appreciate that various modifications, substitutions, omissions and changes may be made without departing from the spirit thereof. Accordingly, it is intended that the scope of the foregoing be limited only by the broadest product statements herein and by the scope of the following claims, including equivalents thereof.

What is claimed is:

1. A method for slowing progression of myopia in a child aged from about 6 to about 18 who is afflicted therewith, said method comprising topically administering to the eyes of said child, at least once per week for a time period of at least one year, an effective amount of at least one compound selected from the group consisting of:
    (a) (2R, 3'R) 3-(2-cyclopentyl-2-phenyl-2-hydroxyacetoxy)-1-(carboxymethyl)-1-methylpyrrolidinium inner salt;
    (b) (2R, 3'S) 3-(2-cyclopentyl-2-phenyl-2-hydroxyacetoxy)-1-(carboxymethyl)-1-methylpyrrolidinium inner salt;
    (c) (2R, 1'R) 3-(2-cyclopentyl-2-phenyl-2-hydroxyacetoxy)-1-(carboxymethyl)-1-methylpyrrolidinium inner salt; and
    (d) (2R, 1'S) 3-(2-cyclopentyl-2-phenyl-2-hydroxyacetoxy)-1-(carboxymethyl)-1-methylpyrrolidinium inner salt;

said at least one compound being optionally administered in the form of an ophthalmic composition comprising said effective amount of said compound and a non-toxic, ophthalmically acceptable carrier.

2. The method according to claim 1, wherein said compound is administered once or twice per day, for from one to seven days per week.

3. The method according to claim 1, carried out for a time period of at least two years.

4. The method according to claim 1, wherein the at least one compound is (2R, 3'R) 3-(2-cyclopentyl-2-phenyl-2-hydroxyacetoxy)-1-(carboxymethyl)-1-methylpyrrolidinium inner salt.

5. The method according to claim 1, wherein said compound is present in said composition in an amount of from about 0.2% w/v to about 1% w/v.

6. A method for treating myopia in a subject afflicted therewith, said method comprising topically administering to the eyes of said subject, at least once per week, an effective amount of at least one compound selected from the group consisting of:
    (a) (2R, 3'R) 3-(2-cyclopentyl-2-phenyl-2-hydroxyacetoxy)-1-(carboxymethyl)-1-methylpyrrolidinium inner salt;
    (b) (2R, 3'S) 3-(2-cyclopentyl-2-phenyl-2-hydroxyacetoxy)-1-(carboxymethyl)-1-methylpyrrolidinium inner salt;
    (c) (2R, 1'R) 3-(2-cyclopentyl-2-phenyl-2-hydroxyacetoxy)-1-(carboxymethyl)-1-methylpyrrolidinium inner salt; and
    (d) (2R, 1'S) 3-(2-cyclopentyl-2-phenyl-2-hydroxyacetoxy)-1-(carboxymethyl)-1-methylpyrrolidinium inner salt;

said at least one compound being optionally administered in the form of an ophthalmic composition comprising said effective amount of said compound and a non-toxic, ophthalmically acceptable carrier.

7. The method according to claim 6, wherein said compound is administered once or twice per day, for from one to seven days per week.

8. The method according to claim 6, wherein the at least one compound is (2R, 3'R) 3-(2-cyclopentyl-2-phenyl-2-hydroxyacetoxy)-1-(carboxymethyl)-1-methylpyrrolidinium inner salt.

9. The method according to claim 6, wherein said compound is present in said composition in an amount of from about 0.2% w/v to about 1% w/v.

10. The method accordingly to claim 2, carried out for a time period of at least two years.

11. The method accordingly to claim 2, wherein the at least one compound is (2R, 3'R) 3-(2-cyclopentyl-2-phenyl-2-hydroxyacetoxy)-1-(carboxymethyl)-1-methylpyrrolidinium inner salt.

12. The method according to claim 3, wherein the at least one compound is (2R, 3'R) 3-(2-cyclopentyl-2-phenyl-2-hydroxyacetoxy)-1-(carboxymethyl)-1-methylpyrrolidinium inner salt.

13. The method according to claim 2, wherein said compound is present in said composition in an amount of from about 0.2% w/v to about 1% w/v.

14. The method according to claim 3, wherein said compound is present in said composition in an amount of from about 0.2% w/v to about 1% w/v.

15. The method according to claim 4, wherein said compound is present in said composition in an amount of from about 0.2% w/v to about 1% w/v.

16. The method accordingly to claim 7, wherein the at least one compound is (2R, 3'R) 3-(2-cyclopentyl-2-phenyl-2-hydroxyacetoxy)-1-(carboxymethyl)-1-methylpyrrolidinium inner salt.

17. The method according to claim 7, wherein said compound is present in said composition in an amount of from about 0.2% w/v to about 1% w/v.

18. The method according to claim 8, wherein said compound is present in said composition in an amount of from about 0.2% w/v to about 1% w/v.

* * * * *